(12) United States Patent
Erskine (10) Patent No.: US 8,021,511 B2
(45) Date of Patent: Sep. 20, 2011

(54) NEEDLE-BASED MEDICAL DEVICE INCLUDING NEEDLE GUIDE AND METHOD FOR CONSTRUCTING

(75) Inventor: Timothy J. Erskine, Sandy, UT (US)

(73) Assignee: Erskine Medical LLC, High Falls, NY (US)

( * ) Notice: Subject to any disclaimer, the term of this patent is extended or adjusted under 35 U.S.C. 154(b) by 214 days.

(21) Appl. No.: 12/245,910

(22) Filed: Oct. 6, 2008

(65) Prior Publication Data

US 2009/0032185 A1 Feb. 5, 2009

Related U.S. Application Data

(62) Division of application No. 11/536,236, filed on Sep. 28, 2006.

(51) Int. Cl.
*B29C 65/00* (2006.01)
*B32B 37/00* (2006.01)
*A61M 5/00* (2006.01)
*A61M 5/31* (2006.01)

(52) U.S. Cl. ......... 156/294; 156/296; 604/187; 604/240

(58) Field of Classification Search .................. 156/242, 156/244.11, 244.13, 244.15, 244.24, 244.25, 156/245, 292, 293, 294, 296, 303.1, 305; 604/187, 240
See application file for complete search history.

(56) References Cited

U.S. PATENT DOCUMENTS

| | | | |
|---|---|---|---|
| 3,096,763 A * | 7/1963 | McConnaughey et al. ... | 604/240 |
| 3,372,697 A * | 3/1968 | Keller ........................... | 604/241 |
| 3,472,227 A | 10/1969 | Burke | |
| 3,523,532 A | 8/1970 | Burke | |
| 3,756,235 A | 9/1973 | Burke et al. | |
| 4,240,425 A | 12/1980 | Akhavi | |
| 6,001,080 A | 12/1999 | Kuracina et al. | |
| 6,004,278 A * | 12/1999 | Botich et al. .................. | 600/576 |
| 6,319,234 B1 * | 11/2001 | Restelli et al. ................ | 604/198 |
| 6,440,104 B1 | 8/2002 | Newby et al. | |
| 6,537,290 B2 | 3/2003 | Adams et al. | |
| 6,605,067 B1 | 8/2003 | Larsen | |
| 7,354,422 B2 | 4/2008 | Riesenberger et al. | |
| 2004/0064107 A1 | 4/2004 | Lo | |

(Continued)

FOREIGN PATENT DOCUMENTS

WO 03028791 A1 4/2003

(Continued)

OTHER PUBLICATIONS

USPTO, Non-final Office Action, U.S. Appl. No. 12/245,914, Apr. 5, 2010.

(Continued)

*Primary Examiner* — Philip C Tucker
*Assistant Examiner* — Brian R Slawski
(74) *Attorney, Agent, or Firm* — Hoffman Warnick LLC (57) ABSTRACT

A needle-based medical device including a needle guide and a method for constructing the same are disclosed. The needle-based medical device includes a tube having a first lumen; a needle guide which is dimensioned to be inserted into the lumen of the tube, and a needle. The needle is inserted such that an end is positioned in the needle guide. A glue may also be provided to secure the needle guide to the tube. In one embodiment, the tube may be made of extruded plastic.

16 Claims, 7 Drawing Sheets

U.S. PATENT DOCUMENTS

| | | |
|---|---|---|
| 2005/0215977 A1 | 9/2005 | Uschold |
| 2006/0047251 A1 | 3/2006 | Smith et al. |
| 2006/0085004 A1 | 4/2006 | Chien |
| 2006/0106340 A1 | 5/2006 | Goossens et al. |

FOREIGN PATENT DOCUMENTS

| | | |
|---|---|---|
| WO | 2007041450 A2 | 4/2007 |

OTHER PUBLICATIONS

USPTO, Final Office Action, U.S. Appl. No. 12/245,910, Apr. 1, 2010.
Erskine, Canadian Intellectual Property, CA Application No. 2,622,403, Office Action dated Dec. 2, 2009, 2 pages.
Erskine, U.S. Appl. No. 11/536,236, Final Office Action Communication, Mar. 26, 2009, 8 pages.
Erskine, U.S. Appl. No. 12/245,914, Office Action Communication, Feb. 9, 2009, 6 pages.
Erskine, U.S. Appl. No. 11/536,236, Office Action Communication, Oct. 6, 2008, 8 pages.
Erskine, U.S. Appl. No. 12/245,914, Office Action Communication, Oct. 1, 2009, 12 pages.
Erskine, U.S. Appl. No. 11/536,236, Office Action Communication, Sep. 16, 2009, 14 pages.
Erskine, U.S. Appl. No. 11/536,236, Office Action Communication, Nov. 13, 2009, 18 pages.
Erskine, Malaysia Application No. PI20080483, Substantive Examination Adverse Report dated Jul. 13, 2009, 3 pages.
International Search Report, WO2007041450, Aug. 8, 2007.
Written Opinion of the International Searching Authority, WO2007041450, Aug. 8, 2007.
International Preliminary Report on Patentability, WO2007041450, Oct. 3, 2008.
Wei State Intellectual Property Office of the People's Republic of China, Notification of the First Office Action for Application No. 200680036099.4 date Oct. 13, 2010, 8 pages.
Suzuki, English Translation of Japanese Notice of Reasons for Rejection for Application No. P2008-533735 dated Oct. 22, 2010, 8 pages.
MacKenzie, Canadian Intellectual Property Office, Office Action Communication for Application Serial No. 2,622,403 dated Dec. 30, 2010, 3 pages.*
Schell, U.S. Appl. No. 12/245,914, Office Action Communication, Oct. 5, 2010, 14 pages.
Schell, U.S. Appl. No. 12/245,914, Office Action Communication, Apr. 29, 2011, 18 pages.
Erskine, Mexian Application No. MX/a/2008/004188, Office Action, dated May 2011, 2 pages.
Erskine, Australian Office Action for U.S. Appl. No. 2006299602 dated Apr. 18, 2011, 4 pages.
Przykutta, Supplementary Partial European Search Report, Application No. EP 06815969, dated May 10, 2011, 11 pages.

* cited by examiner

NEEDLE-BASED MEDICAL DEVICE INCLUDING NEEDLE GUIDE AND METHOD FOR CONSTRUCTING

CROSS-REFERENCE TO RELATED APPLICATION

This application is a divisional patent application of U.S. patent application Ser. No. 11/536,236, filed on Sep. 28, 2006, currently pending.

BACKGROUND OF THE INVENTION

1. Field of the Invention

This patent application relates to medical devices that utilize a needle secured to a hub, including but not limited to catheter assemblies, blood collection devices, huber needle assemblies, syringes, and other needle-based medical devices.

2. Related Art

Current medical devices that include needles are formed by the use of molded tubes, a needle, and a rigid hub to which the needle is secured. The needle hub may be made out of a thin extruded tube or a thin molded tube. Devices of this type are shown in U.S. Provisional Patent Application Nos. 60/659,213, 60/659,217, 60/659,226, and 60/714,954, which are incorporated by reference herein. This method of assembling needle-based medical devices presents several problems associated with the use of molded tubes. One problem is the sheer expense of molding each individual tube used to form a device. The actual manufacture of such devices is also problematic. Molding long, thin members for medical devices with molded tubes is difficult, particularly where the mold core pin must be supported at its distal end. Particularly in small gauge needles, the core pin must have an extremely small diameter, rendering it extremely fragile, difficult to support, and difficult to center. Additionally, each needle size requires a different size core pin to form the needle. In view of the foregoing, there exists a need in the art to overcome one or more of the deficiencies indicated herein.

SUMMARY OF THE INVENTION

A needle-based medical device including a needle guide and a method for constructing the same are disclosed. The needle-based medical device includes a tube having a first lumen; a needle guide which is dimensioned to be inserted into the lumen of the tube, and a needle. The needle is inserted such that an end is positioned in the needle guide. A glue may also be provided to secure the needle guide to the tube. In one embodiment, the tube may be made of extruded plastic.

According to a first aspect of the invention, a needle-based medical device is provided, the medical device comprising: a tube having a first lumen; a needle guide dimensioned to be inserted at least partially into the first lumen, the needle guide including a second lumen and a glue well; a needle having an end in the second lumen; and glue to secure the needle guide to the tube.

According to a second aspect of the invention, a method of constructing a needle-based medical device is provided, the method comprising: providing a tube having a first lumen; providing a needle guide; inserting the needle guide into the first lumen; inserting a needle into the needle guide; introducing glue into a glue well between the needle guide and the first lumen; and curing the glue.

According to a third aspect of the invention, a needle guide for a needle-based medical device is provided, the needle guide comprising: a body for insertion into a first lumen of a tube, the body including a second lumen to position an end of a needle.

According to a fourth aspect of the invention, a needle hub for a needle-based medical device is provided, the needle hub comprising: a tube having a first lumen; a needle guide having an outer surface for engaging the inner surface and a second lumen for positioning a needle; and a glue for hermetically sealing the needle, the tube, and the needle guide.

BRIEF DESCRIPTION OF THE DRAWINGS

These and other features of this invention will be more readily understood from the following detailed description of the various aspects of the invention taken in conjunction with the accompanying drawings, in which.

It is noted that the drawings of the invention are not necessarily to scale. The drawings are merely schematic representations, not intended to portray specific parameters of the invention. The drawings are intended to depict only typical embodiments of the invention, and therefore should not be considered as limiting the scope of the invention. In the drawings, like numbering represents like elements.

DETAILED DESCRIPTION

A device and a method are disclosed that provide an improved method of producing needle-based medical devices more effectively and efficiently.

Figure 1:
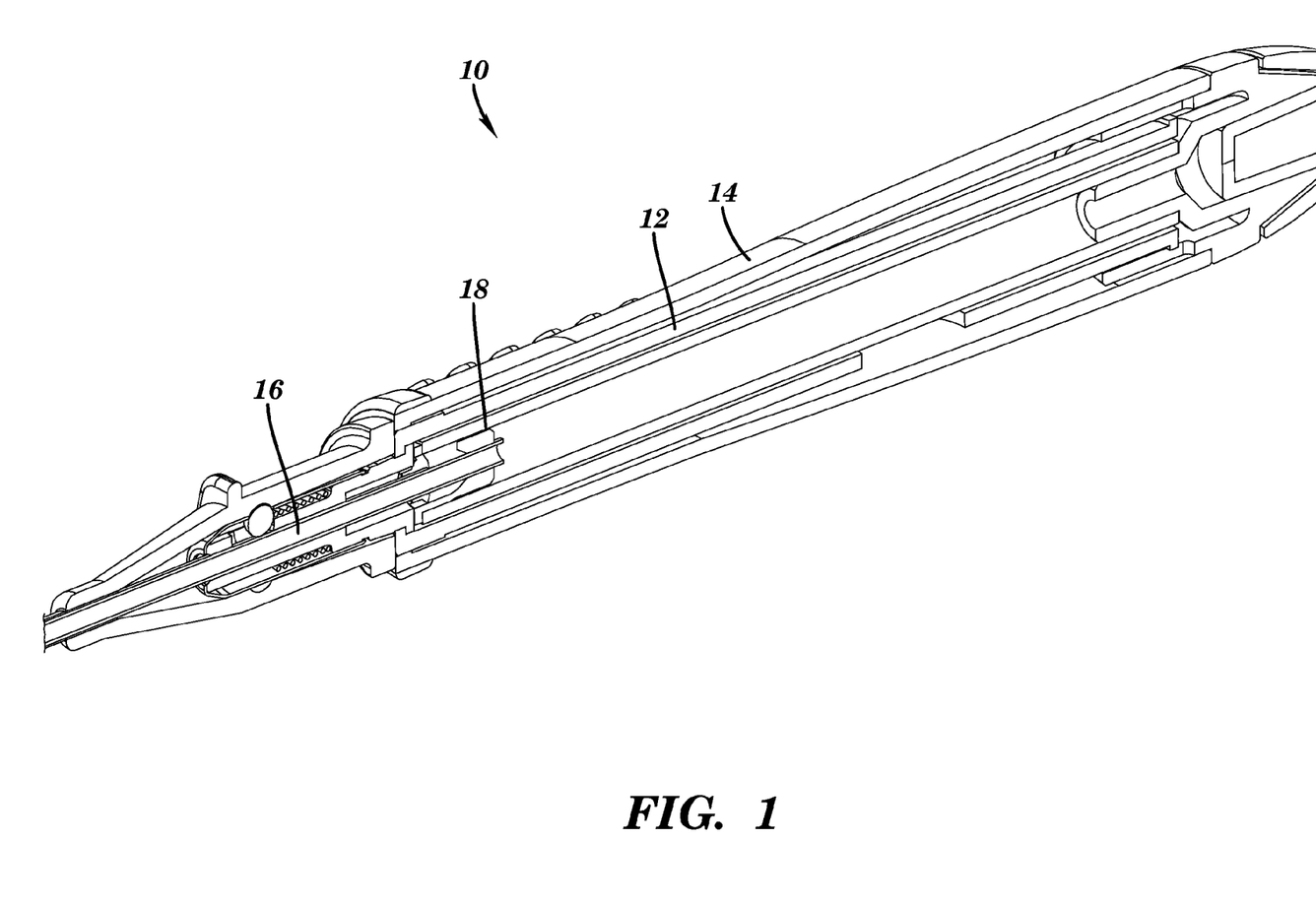
FIG. 1 depicts an isometric cross-sectional view of a medical device (a catheter introducer) embodying one embodiment of the invention.

Referring now to FIG. 1, one embodiment of a needle-based medical device 10 is shown in the form of, for example, a catheter introducer 10 with a needle shield 12, including components made from concentric extruded tubes 12, 14, and 18. These concentric tubes include needle shield 12, outer housing 14, and needle hub 18. The use of extrusions substantially reduces the cost of such devices compared with existing devices made out of molded parts, although molded tubes may be used. Although medical device 10 is described herein as a catheter introducer assembly, it is understood that the teachings of the invention are applicable to any type of needle-based device, including but not limited to catheter introducers, blood collection devices, huber needle assemblies, and syringes.

Figure 2:
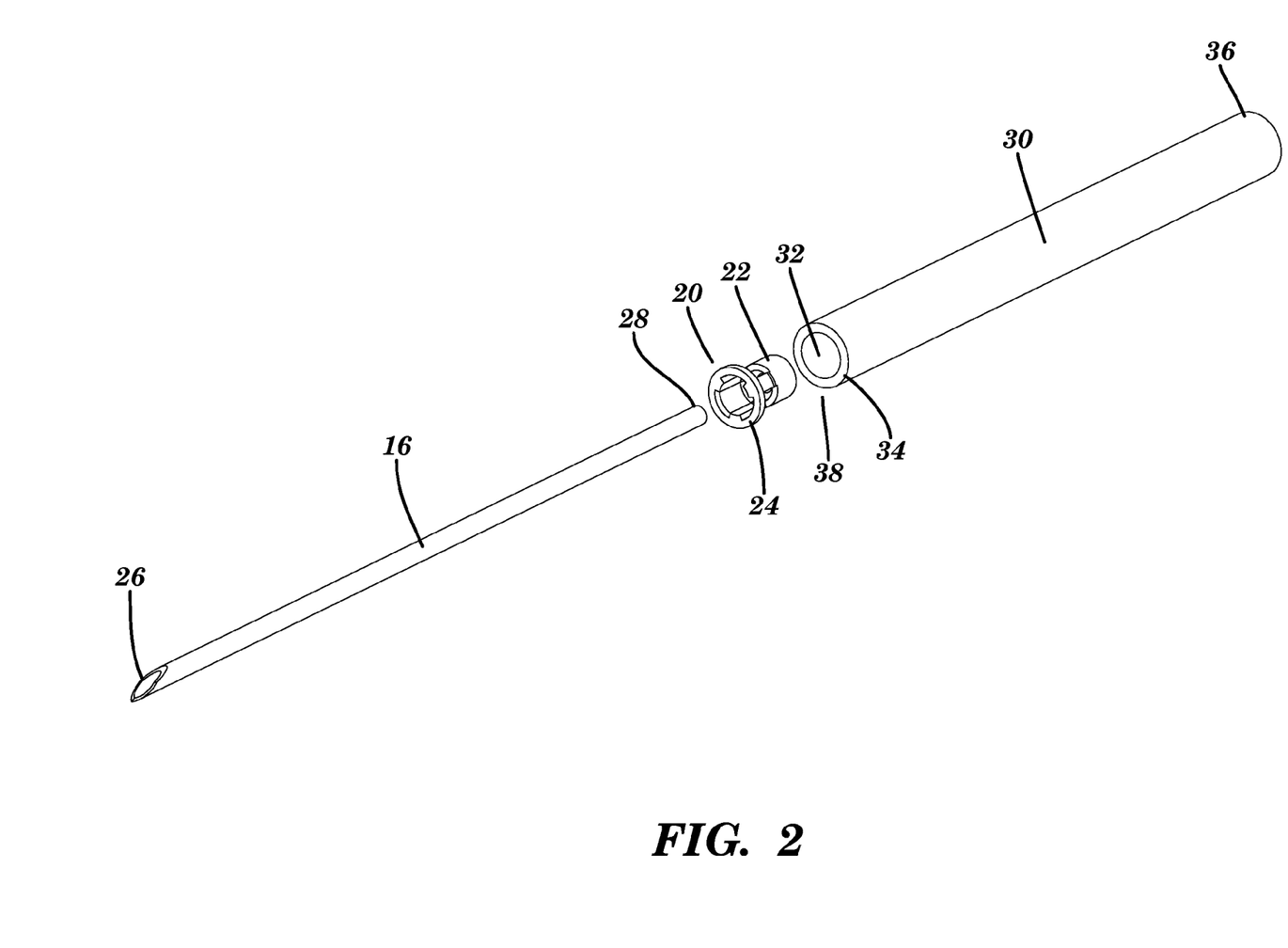
FIG. 2 depicts an exploded view of a needle hub embodying one embodiment of the invention.

Referring now to FIG. 2, tube 30, needle guide 20, and needle 16 are shown in an exploded view. Needle 16 has a distal end 26 and a proximal end 28, and is secured to needle guide 20. Needle guide 20 is secured to tube 30, forming the needle and hub for a needle-based medical device 10 (FIG. 1). Body 22 of needle guide 20 is inserted into distal end 38 of tube 30. Proximal end 28 of needle 16 is inserted into body 22 of needle guide 20. Tube 30 may be, for example, a plastic extrusion made of polypropylene, acrylic, or other similar material, and has a proximal end 36, a distal end 38, and a first lumen 32 extending between proximal end 36 and distal end 38.

Figure 3:
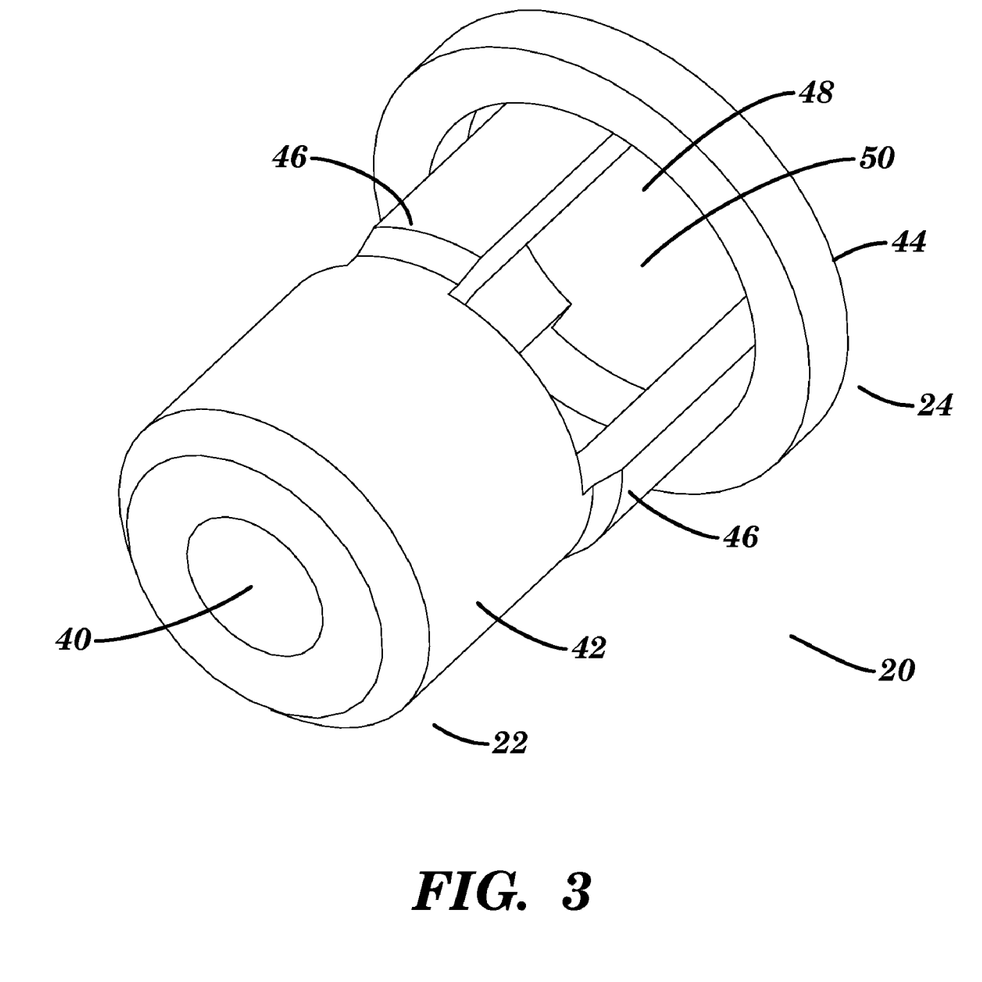
FIG. 3 depicts an isometric view of the needle guide showing a glue well.

Referring now to FIG. 3, a more detailed view of needle guide 20 is provided. In one embodiment, needle guide 20 includes a body 22 for insertion into first lumen 32 (FIG. 2) of tube 30 (FIG. 2). Body 22 may include a second lumen 40 to position an end 28 (FIG. 2) of needle 16. In one embodiment, body 22 is generally cylindrical and further includes an outer surface 42. Body 22 is joined to distal end 38 by at least one rib 46 which extends from body 22. In one embodiment, the number of ribs may be three, and each of three ribs 46 may be positioned approximately 120 degrees from each other rib 46. It is understood, however, that any number of ribs greater than one may be used. As will be described herein, empty spaces 48 lie between ribs 46, in a configuration which forms a glue well 50 adjacent to the at least one rib 46 and first lumen 32 (FIG. 2), and includes a space between proximal end 28 of needle 16 and second lumen 40.

Figure 4:
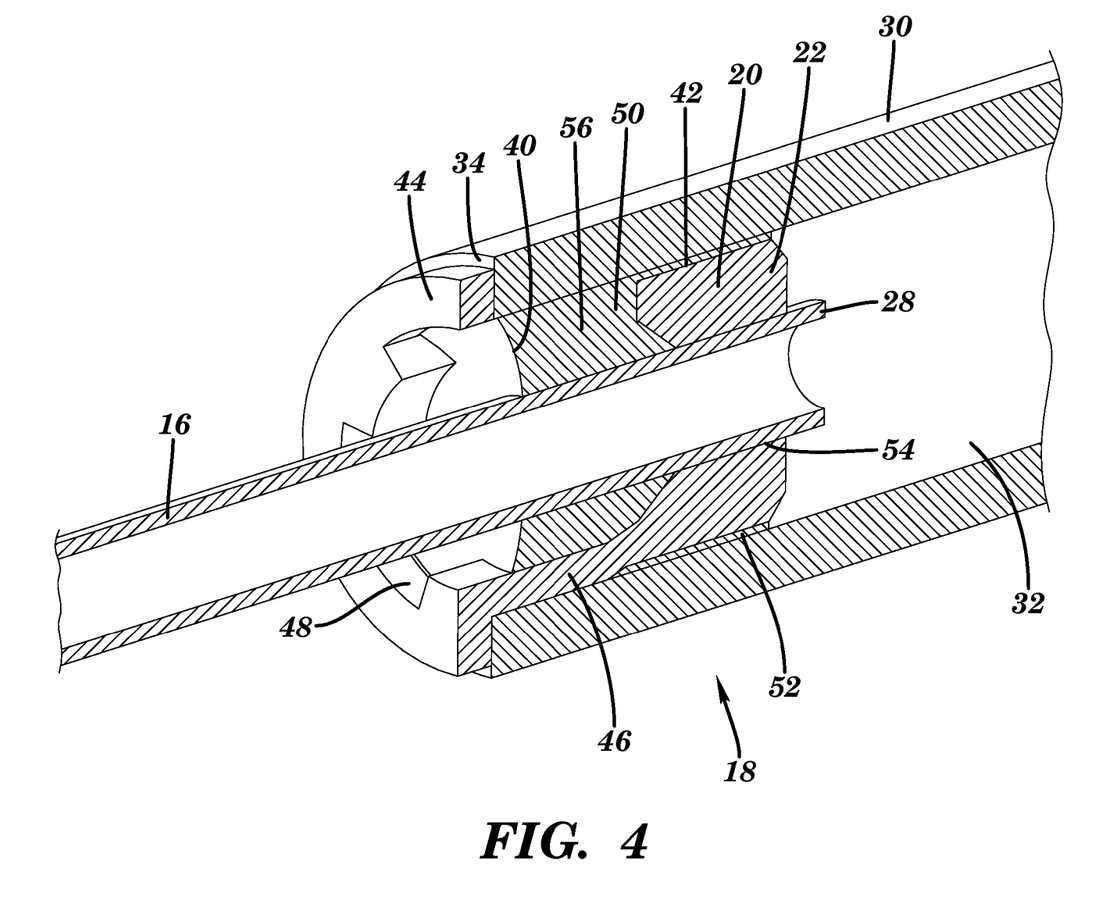
FIG. 4 depicts an isometric cross-sectional view showing the assembled needle hub.

Referring now to FIG. 4, a first embodiment of an assembled needle hub is depicted, including tube 30 having first lumen 32, needle guide 20 dimensioned to be inserted at least partially into first lumen 32. Needle 16 has proximal end 28 in second lumen 40, and a glue 56 is positioned to secure needle guide 20 to tube 30. Proximal end 28 of needle 16 is inserted into second lumen 40 in needle guide 20, the second lumen having a diameter slightly larger than that of needle 16. In one embodiment, a friction fit is provided between second lumen 40 and proximal end 28 of needle 16, maintaining substantially circumferential contact between the second lumen 40 and the needle 16.

Body 22 of needle guide 20 is inserted into first lumen 32 such that it is positioned coaxially with tube 30. Needle guide 20 may include a flange 44 coupled to at least one rib 46 at a distal end of needle guide 20, which is positioned to engage with outer wall 34 of tube 30 when body 22 is inserted into first lumen 32. Flange 44 thus acts as a mechanical stop, limiting the depth to which body 22 can be inserted into first lumen 32. The ribs 46 have a diameter just smaller than the diameter of first lumen 32, which provides a mechanical fit between body 22 and first lumen 32.

When body 22 is inserted into first lumen 32, first annular space 52 is formed between the inner wall of tube 30 and outer surface 42 of body 22. This space ideally measures about 0.001-0.005 inch, which allows glue 56 to flow via capillary action into first annular space 52 after it is deposited in glue well 50. A very tight fit of ribs 46 is not preferred because that may cause distortion of distal end 38 of tube 30. In one embodiment, a second annular space 54 is formed between second lumen 40 and the outer surface of proximal end 28 of needle 16. In this embodiment, annular space 54 is also filled with glue as part of glue well 50 by capillary action; however, second annular space 54 is not essential to the practice of the claimed invention.

Figure 5:
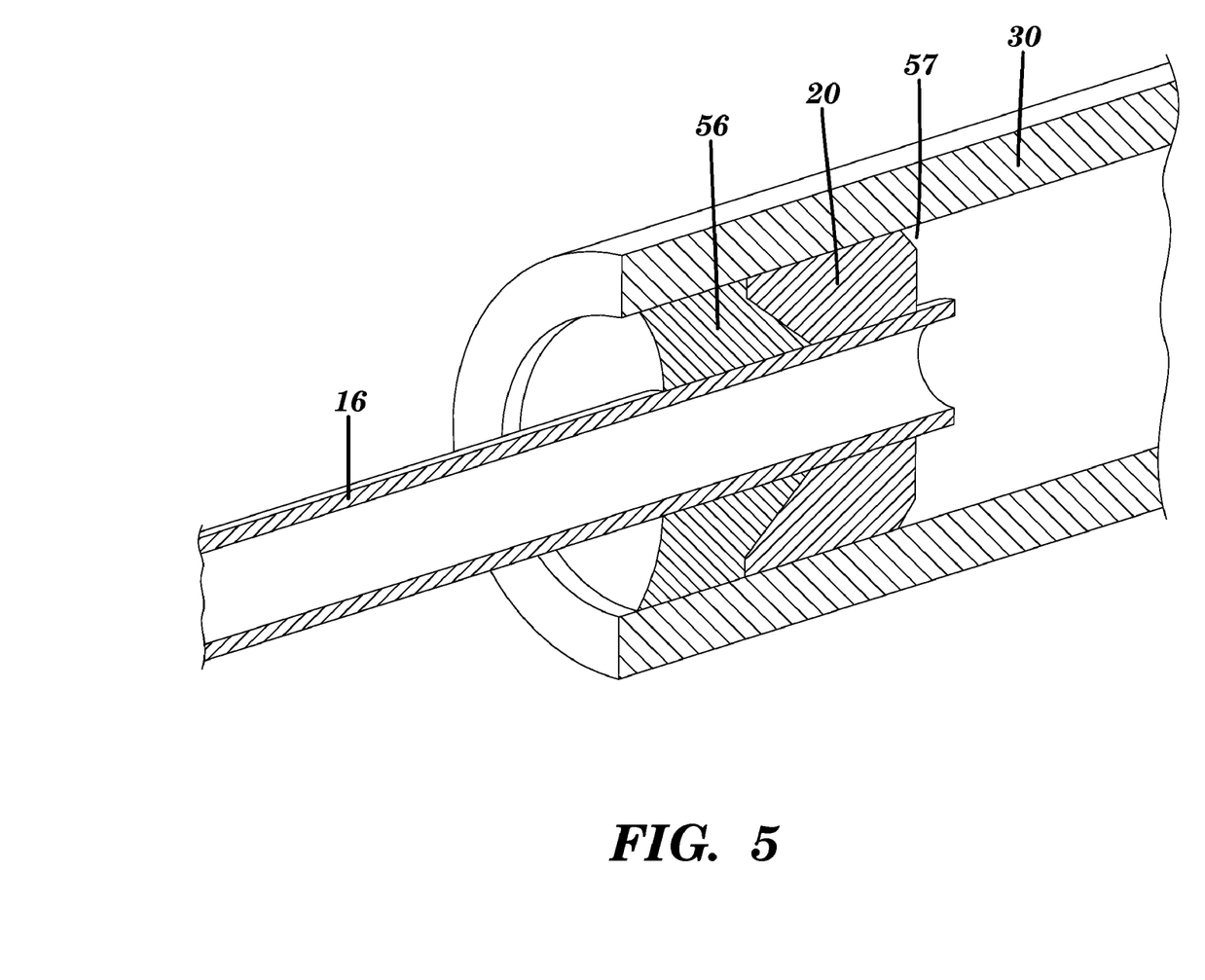
FIG. 5 depicts an isometric cross-sectional view showing an alternative embodiment of the assembled needle hub.

Referring now to FIG. 5, a second embodiment of the assembled needle hub is depicted. According to this embodiment, needle 16 can be pre-molded into needle guide 20 and then inserted into first lumen 32. The inner surface of tube 20 may include a depth stop to limit axial movement of the needle guide relative to the tube. The depth stop may be an abutment 57 positioned on the inner surface of tube 30. Returning to FIG. 1, once needle hub 18 has been assembled, it can be used in a device such as the catheter inserter or any similar needle-based device. Needle hub 18 may also be assembled during assembly of such devices.

A first embodiment of a method of constructing a needle-based medical device is provided wherein the device is assembled as follows. Tube 30 having first lumen 32 is provided along with needle guide 20. Needle guide 20, e.g., body 22 of needle guide 20, is inserted into first lumen 32 until flange 44 abuts outer wall 34 of tube 30, preventing further insertion. Proximal end 28 of needle 16 is then inserted into second lumen 40 from distal end 24 of guide 20. Glue 56 is introduced into glue well 50, and then flows by capillary action into first annular space 52 between outer surface 42 of body 22 of guide 20 and inner wall of tube 30. In an embodiment including second annular space 54, glue 56 is also allowed to flow into second annular space 54 between needle 16 and body 22 of guide 20. Glue 56 is then cured.

A second embodiment of a method of constructing a needle-based medical device is provided wherein the proximal end 28 of needle 16 is inserted into second lumen 40 from distal end 24 of needle guide 20 before body 22 is inserted into first lumen 32. In that case, the coefficient of friction between needle 16 and guide 20 must be greater than the coefficient of friction between guide 20 and tube 30. In an alternative embodiment, a press fit or serrations in needle guide 20 may be provided to hold needle guide 20 in place against the force of insertion of needle 16.

Figure 6:
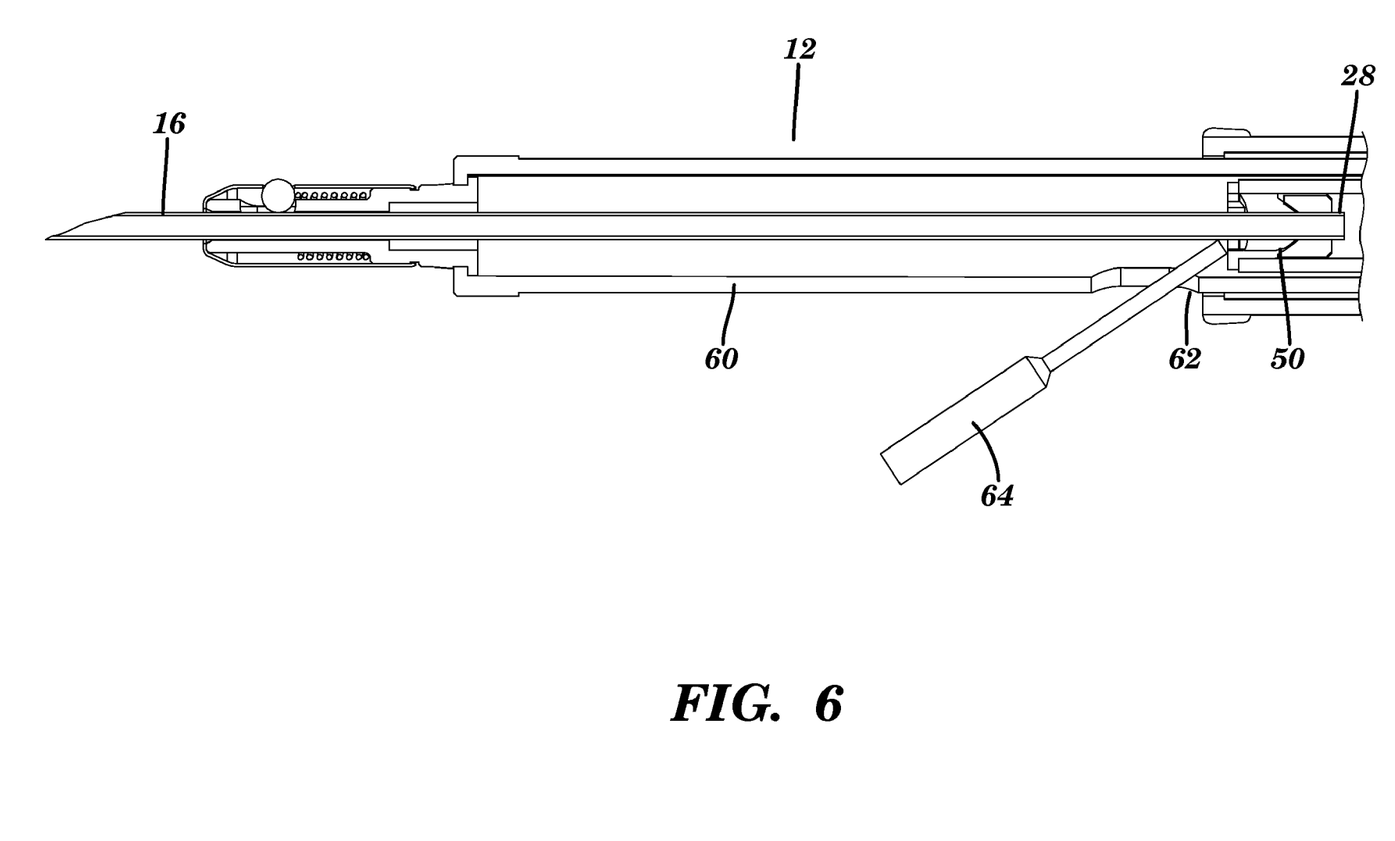
FIG. 6 depicts an orthogonal cross-sectional view of the device shown in FIG. 1 showing one embodiment of accessing the glue well during manufacture.

Referring now to FIG. 6, a first embodiment of accessing glue well 50 during manufacture is provided. According to this embodiment, needle shield 12 may be threaded onto needle 16 from proximal end 28 (the blunt end) of needle 16. In that case, access to glue well 50 may be obtained via a cutout 62 in needle shield 12. Glue nozzle 64 is inserted into cutout 62 and introduces glue 56 into glue well 50.

Figure 7:
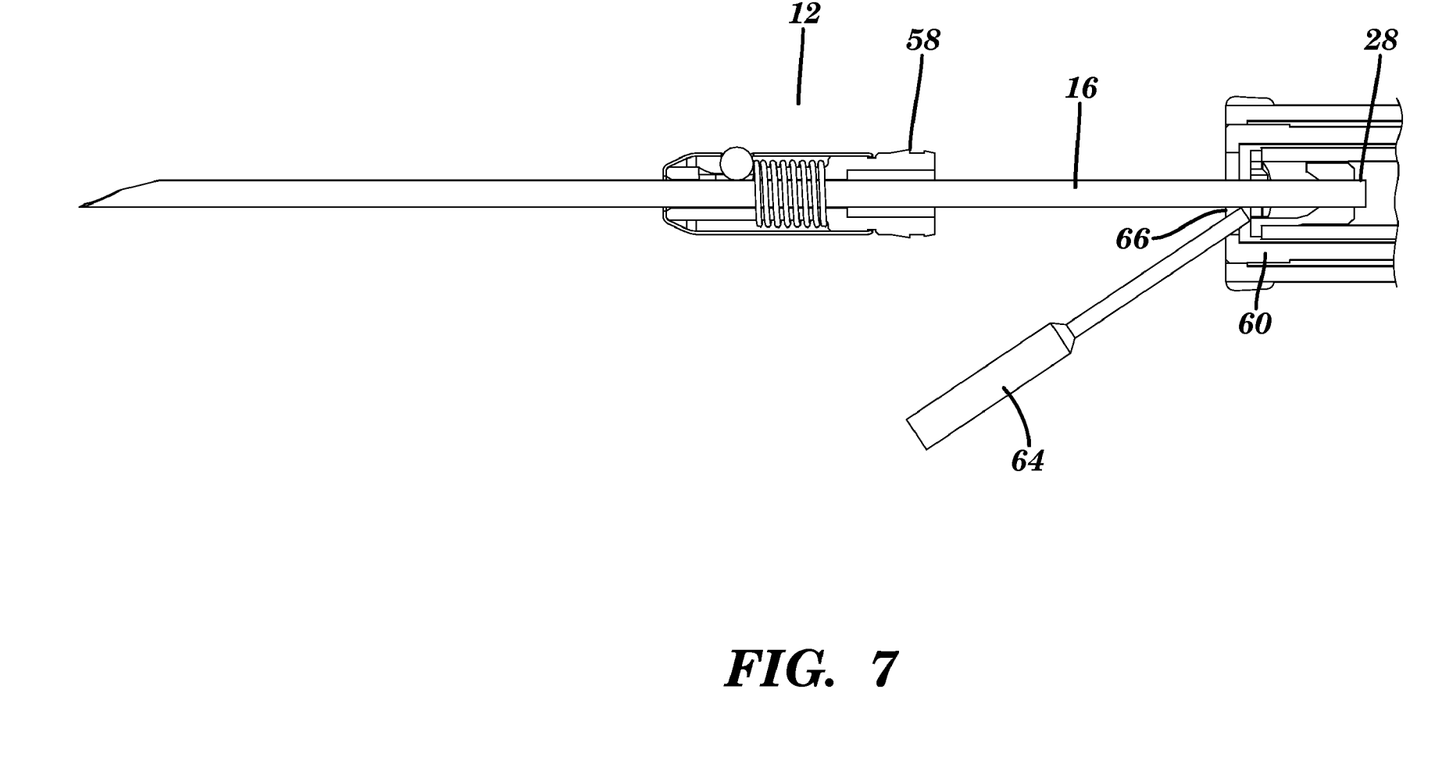
FIG. 7 depicts an orthogonal cross-sectional view of the device shown in FIG. 1 showing another embodiment of accessing the glue well during manufacture.

Referring now to FIG. 7, a second embodiment for accessing glue well 50 during manufacture is depicted. According to this embodiment, access to glue well 50 is provided while keeping distal end 58 of needle shield 12 separate from needle shield body 60 (but still threaded on needle 16) during the gluing process. In that case, glue nozzle 64 is inserted into the end of lumen 66 of needle shield body 60. Glue 56 is introduced into glue well 50, after which, distal end 58 of needle shield 12 is snapped and bonded or otherwise attached to needle shield body 60.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of the invention as defined by the accompanying claims.

What is claimed is:

1. A method of constructing a needle-based medical device, the method comprising:
   providing a tube having a distal end and a proximal end, and a first lumen extending between the distal end and the proximal end;
   providing a needle guide,
      wherein the needle guide includes a body having an outer surface at a first radial distance from a longitudinal axis of the body, and at least one rib extending longitudinally in a distal direction from the body, and
      wherein the at least one rib is fixedly distanced from the longitudinal axis of the body by a second radial distance, the second radial distance being greater than the first radial distance;
   inserting the needle guide into the distal end of the first lumen such that the at least one rib engages the first lumen;

inserting a proximal end of a needle into the needle guide, such that a sharp tip of the needle extends distally of the needle guide;

introducing glue into a glue well between the needle guide and the first lumen; and curing the glue.

2. The method of claim 1, wherein the glue well includes a first annular space between the body of the needle guide and the first lumen.

3. The method of claim 2, wherein the glue well further includes a second annular space between the needle and the needle guide.

4. The method of claim 1, wherein the glue well is adjacent to the at least one rib and the first lumen.

5. The method of claim 1, wherein the inserting includes inserting the needle guide into the tube until the needle guide abuts the distal end of the tube.

6. The method of claim 1, further comprising providing a depth stop to limit the depth to which the needle guide is inserted into the tube.

7. The method of claim 1, wherein the needle inserting occurs prior to the inserting of the needle guide into the tube.

8. The method of claim 1, wherein the needle inserting occurs after the inserting of the needle guide into the tube.

9. The method of claim 1, wherein the tube is an extruded or molded tube.

10. The method of claim 1, further comprising providing a friction fit between the needle and the needle guide.

11. The method of claim 1, further comprising threading a needle shield over the needle.

12. The method of claim 1, further comprising providing a needle shield with an opening to give access to the first lumen for the glue introducing.

13. The method of claim 1, further comprising press-fitting the needle guide into the tube.

14. The method of claim 1, wherein the at least one rib further comprises at least two ribs.

15. The method of claim 14, wherein the at least two ribs further comprises a first rib, a second rib, and a third rib, wherein each of the first, second, and third ribs are spaced apart from each other by about 120 degrees.

16. The method of claim 3, wherein the glue well further comprises a hermetic seal between the needle and the first lumen.

* * * * *